(12) United States Patent
Takahashi et al.

(10) Patent No.: US 10,064,763 B2
(45) Date of Patent: Sep. 4, 2018

(54) ABSORBENT ARTICLE WITH ELASTIC MEMBERS

(71) Applicant: LIVEDO CORPORATION, Ehime (JP)

(72) Inventors: Yuki Takahashi, Tokushima (JP); Emi Amano, Tokushima (JP); Tomohito Uda, Osaka (JP)

(73) Assignee: LIVEDO CORPORATION, Ehime (JP)

( * ) Notice: Subject to any disclaimer, the term of this patent is extended or adjusted under 35 U.S.C. 154(b) by 777 days.

(21) Appl. No.: 14/368,987

(22) PCT Filed: Nov. 29, 2012

(86) PCT No.: PCT/JP2012/080876
§ 371 (c)(1),
(2) Date: Jun. 26, 2014

(87) PCT Pub. No.: WO2013/099510
PCT Pub. Date: Jul. 4, 2013

(65) Prior Publication Data
US 2014/0358110 A1   Dec. 4, 2014

(30) Foreign Application Priority Data

Dec. 28, 2011   (JP) .................................. 2011-287454

(51) Int. Cl.
*A61F 13/15*   (2006.01)
*A61F 13/20*   (2006.01)
(Continued)

(52) U.S. Cl.
CPC ...... *A61F 13/49011* (2013.01); *A61F 13/496* (2013.01); *A61F 13/49058* (2013.01);
(Continued)

(58) Field of Classification Search
CPC .. A61F 2013/49028; A61F 2013/49026; A61F 13/49011; A61F 13/496
See application file for complete search history.

(56) References Cited

U.S. PATENT DOCUMENTS

2002/0147439 A1* 10/2002 Tanaka .................. A61F 13/496
604/398
2003/0022582 A1   1/2003 Cree et al.
(Continued)

FOREIGN PATENT DOCUMENTS

EP   0806196 A2   11/1997
EP   0806196 A3   3/1999
(Continued)

OTHER PUBLICATIONS

International Preliminary Report on Patentability for PCT Patent App. No. PCT/JP2012/080876 (dated Jul. 1, 2014) with English language translation thereof.
(Continued)

*Primary Examiner* — Michele M Kidwell
(74) *Attorney, Agent, or Firm* — Cermak Nakajima & McGowan LLP; Tomoko Nakajima (57) ABSTRACT

A pants-type disposable diaper includes a pair of strip projecting parts projecting laterally from a line of connection between front and rear parts located respectively on the belly and back sides of a wearer, a first waist elastic member joined to a first waist region that is an upper part of a waist region extending along a waist opening, and a second waist elastic member joined to a second waist region that is a lower part of the waist region. In a state in which an outer covering sheet is elongated in a right-left direction, a first unit contractile force that is a contractile force in the right-left direction per unit width of the first waist region in
(Continued)

an up-down direction is smaller than a second unit contractile force in the second waist region.

14 Claims, 3 Drawing Sheets

(51) Int. Cl.
*A61F 13/49* (2006.01)
*A61F 13/496* (2006.01)

(52) U.S. Cl.
CPC .............. *A61F 2013/49041* (2013.01); *A61F 2013/49088* (2013.01); *A61F 2013/49092* (2013.01)

(56) References Cited

U.S. PATENT DOCUMENTS

| | | |
|---|---|---|
| 2004/0102757 A1 | 5/2004 | Olson |
| 2005/0107764 A1 | 5/2005 | Matsuda et al. |
| 2005/0177124 A1* | 8/2005 | Kondo ............... A61F 13/42 604/385.29 |
| 2008/0027406 A1 | 1/2008 | Shirai et al. |
| 2009/0030392 A1 | 1/2009 | Kanai et al. |
| 2009/0088718 A1 | 4/2009 | Toyoshima et al. |
| 2009/0131896 A1 | 5/2009 | Ebitsuka et al. |
| 2010/0106123 A1* | 4/2010 | Fukae ............... A61F 13/49015 604/373 |
| 2010/0228218 A1 | 9/2010 | Langdon et al. |
| 2011/0098666 A1 | 4/2011 | Nakajima et al. |
| 2011/0106039 A1 | 5/2011 | Saito et al. |
| 2011/0178489 A1 | 7/2011 | Baba et al. |
| 2012/0083757 A1 | 4/2012 | Takahashi et al. |
| 2012/0116343 A1* | 5/2012 | Yoshioka ............. A61F 13/496 604/385.29 |

FOREIGN PATENT DOCUMENTS

| | | |
|---|---|---|
| EP | 1661538 A1 | 5/2006 |
| JP | 2001-178770 A | 7/2001 |
| JP | 2006-061682 A | 3/2006 |
| JP | 2007-97643 A | 4/2007 |
| JP | 2007-143874 A | 6/2007 |
| JP | 2007-195647 A | 8/2007 |
| JP | 2008-543525 A | 12/2008 |
| JP | 2009-18095 A | 1/2009 |
| JP | 2009-125087 A | 6/2009 |
| JP | 2009-125088 A | 6/2009 |
| JP | 2009-240694 A | 10/2009 |
| JP | 2010-069023 A | 4/2010 |
| JP | 2010-273962 A | 12/2010 |
| JP | 4943158 B2 | 3/2012 |
| KR | 10-2007-0086694 A | 8/2007 |
| KR | 10-2008-0007475 A | 1/2008 |
| KR | 10-2011-0021992 A | 3/2011 |

OTHER PUBLICATIONS

International Search Report for PCT Patent App. No. PCT/JP2012/080876 (dated Jan. 29, 2013).
Written Opinion for PCT Patent App. No. PCT/JP2012/080876 (dated Jan. 29, 2013).
Notice of Decision to Grant a Patent for Korean Patent App. No. 10-2014-7019147 (dated Sep. 22, 2015).
Supplementary European Search Report for European Patent App. No. 12861239.7 (dated Aug. 10, 2015).
Notice of Decision to Grant a Patent from Taiwanese Patent App. No. 101144927 (dated Nov. 6, 2014).

* cited by examiner

ABSORBENT ARTICLE WITH ELASTIC MEMBERS

This application is a national phase entry under 35 U.S.C. § 371 of PCT Patent Application No. PCT/JP2012/080876, filed on Nov. 29, 2012, which claims priority under 35 U.S.C. § 119 to Japanese Patent Application No. 2011-287454, filed Dec. 28, 2011, both of which are incorporated by reference.

TECHNICAL FIELD

The present invention relates to a pants-type absorbent article.

BACKGROUND ART

Pants-type disposable diapers having a waist opening at the top end and a pair of leg openings in the lower portion have conventionally been used as one type of absorbent articles for receiving body waste discharged from a wearer. In front and rear parts of a pants-type disposable diaper that are located respectively on the belly and back sides of the wearer, a waist elastic member is provided along the edge of the waist opening. In a crotch part located between the front and rear parts, leg elastic members are provided along the edges of the pair of leg openings. In the front and rear parts, a middle elastic member is also provided between the waist elastic member and the leg elastic members in an up-down direction.

In a pants-type disposable diaper disclosed in Japanese Patent Application Laid-Open No. 2009-240694 (Document 1), front and rear parts located on the belly and back sides of a wearer are divided into a first expansible region that is located in the vicinity of the edge of a waist opening, a second expansible region that is located adjacent to the first expansible region and crosses a front end portion of an absorptive chassis, and third expansible regions that are located adjacent to the second expansible region and on both sides of the absorptive chassis. Setting the elongation stress of the second expansible region to be equal to or greater than that of the first expansible region suppresses the formation of creases in the second expansible region and the front end portion of the absorptive chassis due to the effect of elongation of the first expansible region when the wearer bends forward.

In pants-type absorbent articles disclosed in Japanese Patent Application Laid-Open Nos. 2009-125088 (Document 2) and 2009-125087 (Document 3), front and rear parts are divided into four strip-like regions of the same width that extend in the width direction, the four strip-like regions being referred to respectively as a first region, a second region, a third region, and a fourth region in order from the top. In the pants-type absorbent article disclosed in Document 2, the contractile forces in the respective regions are set such that the second region has a greater contractile force than those of the first and third regions, and the fourth region has a greater contractile force than that of the third region. In this way, setting a greater contractile force in the second and fourth regions where the wearer has bones that protrude to the surface of his or her body suppresses slipping off of the absorbent article, and setting a smaller contractile force in the first region that shifts greatly due to movement of the wearer makes the absorbent article more comfortable to wear. In Document 3, which aims to provide a pants-type disposable diaper capable of preventing slipping-off and being very comfortable to wear, the second and fourth regions are set to have an average contractile force greater than that of the third region, the fourth region on the belly side is set to have a contractile force greater than that of the forth region on the back side, and the second region is set to have an average contractile force greater than that of the first region.

In a disposable diaper disclosed in Japanese Patent Application Laid-Open No. 2010-69023 (Document 4), a front part is divided from the waist opening side into a first expansible region, a second expansible region, and a third expansible region, a rear part is divided from the waist opening side into a fourth expansible region, a fifth expansible region, and a sixth expansible region, and the elongation stresses of the respective expansible regions has the following correlation: sixth expansible region>second expansible region>third expansible region≥fifth expansible region>first expansible region, and sixth expansible region>second expansible region>third expansible region fifth expansible region>fourth expansible region.

In a pants-type disposable diaper disclosed in Japanese Patent Application Laid-Open No. 2001-178770 (Document 5), front and rear parts are divided from the waist opening side into a waist section, an upper side section, and a lower side section, and elastic expansion forces of the respective sections has the following correlation: lower side section≥upper side section>waist section.

In a pants-type disposable diaper disclosed in Japanese Patent Application Laid-Open No. 2006-61682 (Document 6), when the disposable diaper is worn, a first region located between a waist opening and leg openings has the highest pressure applied thereto, the waist opening has the second highest pressure applied thereto, and a second region located between the first region and the leg openings has the lowest pressure applied thereto. Such a structure not only effectively prevents the diaper slipping off when being worn, but also effectively prevents liquid leakage because the diaper fits the body of a wearer closely without discomfort.

Incidentally, in pants-type disposable diapers, a pair of strip projecting parts, each projecting laterally from a line of connection between front and rear parts, is formed when the front and rear parts are joined to each other on both right and left sides. The strip projecting parts are less flexible than the other parts of the disposable diaper because they are formed by joining laminated sheet members such as nonwoven fabric by thermal compression bonding, for example. Thus, in a state where the disposable diaper is worn, the upper end portions of the strip projecting parts may cut into the body of the wearer and make the wearer uncomfortable due to contraction of a waist elastic member provided in a waist region extending along the edge of the waist opening.

Documents 1 to 6 have proposed to reduce the contractile force in the waist region to smaller than that in the other region, but it is necessary to maintain the contractile force in the waist region at a certain level or higher in order to prevent the disposable diaper from slipping off the wearer. Thus, with the structures as disclosed in Documents 1 to 6, the upper end portions of the strip projecting parts will still cut into the body of a wearer.

SUMMARY OF INVENTION

The present invention is intended for a pants-type absorbent article, and it is an object of the present invention to suppress cutting in of the upper end portions of the strip projecting parts into the body of a wearer.

The absorbent article according to the present invention includes an outer covering sheet having a waist opening at an upper end and a pair of leg openings in a lower portion, and an absorbent body attached to a wearer side of the outer covering sheet to absorb body waste discharged from a wearer. The outer covering sheet includes a front part to be located on a belly side of the wearer, a rear part to be located on a back side of the wearer, both side ends of the rear part being connected to both side ends of the front part, a crotch part continuous with the front part and the rear part, a pair of strip projecting parts formed by joining inner surfaces of areas of the front part that are laterally continuous with both of the side ends of the front part and inner surfaces of areas of the rear part that are laterally continuous with both of the side ends of the rear part, each of the pair of strip projecting parts having a strip-like shape that extends in an up-down direction and projecting laterally from a line of connection between the front part and the rear part, a waist elastic member joined to the front part and the rear part in a waist region located along an edge of the waist opening, and configured to contract to form a waist opening gather, leg elastic members joined to the crotch part along edges of the pair of leg openings and configured to contract to form a pair of leg opening gathers, and a middle elastic member joined to the front part and the rear part in a space in the up-down direction between the waist elastic member and the leg elastic members, and configured to contract to form a middle gather. The waist elastic member includes a first waist elastic member disposed approximately in parallel with the edge of aid waist opening in a first waist region that is an upper part of the waist region, and a second waist elastic member disposed approximately in parallel with the first waist elastic member in a second waist region that is a region of the waist region below the first waist region. In a state in which the outer covering sheet is elongated in a right-left direction perpendicular to the up-down direction, a first unit contractile force that is a contractile force in the right-left direction per unit width of the first waist region in the up-down direction is smaller than a second unit contractile force that is a contractile force in the right-left direction per unit width of the second waist region in the up-down direction.

According to the present invention, it is possible to suppress cutting in of the upper end portions of the strip projecting parts into the body of a wearer.

Preferably, the waist region is located above an upper end of the absorbent body. In addition, the waist region has a width of 50 mm or less in the up-down direction.

In a preferred embodiment of the present invention, the outer covering sheet includes a folded portion formed by folding the outer covering sheet toward a wearer at the edge of the waist opening, and the waist elastic member is disposed between the folded portion and a portion of the outer covering sheet that faces the folded portion. Accordingly, the upper end portions of the strip projecting parts are formed by the fold in the continuous sheet member. It is thus possible to further suppress cutting in of the upper end portions of the strip projecting parts into the body of a wearer, as compared with the case in which a cut edge of the sheet member forms the upper end portions of the strip projecting parts.

In another preferred embodiment of the present invention, the waist region is formed by laminating a plurality of sheet members, and the number of sheet members in the first waist region is less than the number of sheet members in the second waist region. Accordingly, it is possible to further suppress cutting in of the upper end portions of the strip projecting parts into the body of a wearer.

In one aspect of the present invention, the outer covering sheet includes an auxiliary region between the second waist region and a middle elastic region in which the middle elastic member is disposed, and in a state in which the outer covering sheet is elongated in the right-left direction, a contractile force in the right-left direction per unit width of the auxiliary region in the up-down direction is smaller than any of a contractile force in the right-left direction per unit width of the middle elastic region in the up-down direction, the first unit contractile force, and the second unit contractile force. This makes it easy to firmly grasp the absorbent article by hooking fingers deep into the auxiliary region, enabling the absorbent article to be readily moved along the body of a wearer.

These and other objects, features, aspects and advantages of the present invention will become more apparent from the following detailed description of the present invention when taken in conjunction with the accompanying drawings.

DESCRIPTION OF EMBODIMENT

Figure 1:
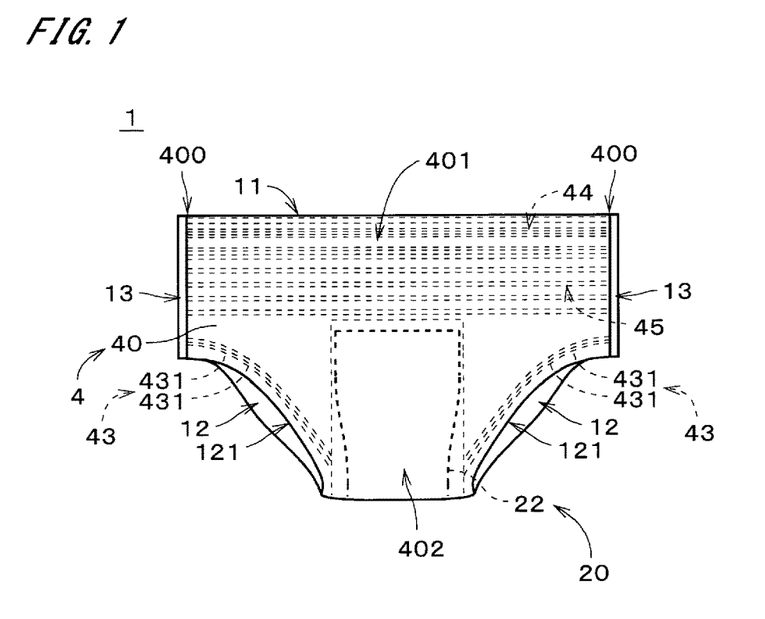
FIG. 1 is a front view of a disposable diaper according to an embodiment.
Figure 2:
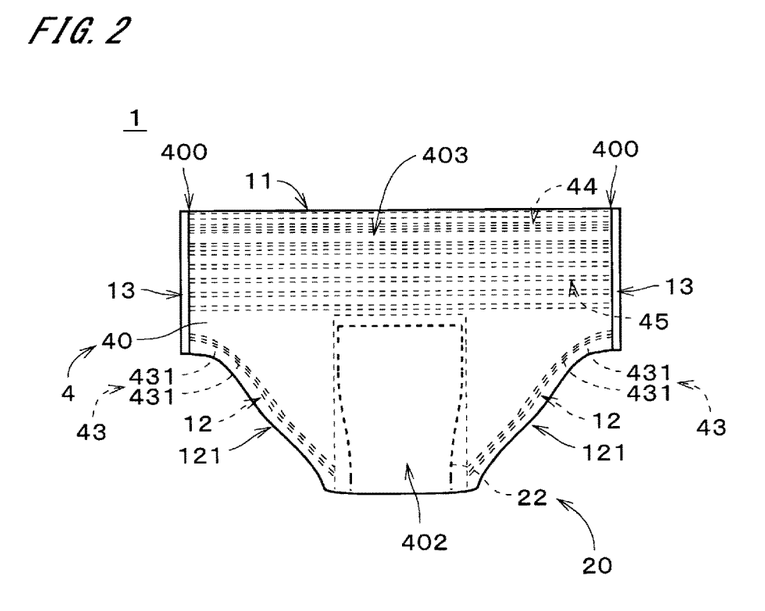
FIG. 2 is a rear view of the disposable diaper.

FIGS. 1 and 2 are respectively front and rear views of a disposable diaper 1 according to an embodiment of the present invention (i.e., views of areas located respectively on the belly and back sides of a wearer). As shown in FIGS. 1 and 2, the disposable diaper 1 is a pants-type absorbent article having a waist opening 11 at the upper end (i.e., the end on the upper side in FIGS. 1 and 2) and a pair of leg openings 12 in the lower portion, and is configured to receive body waste discharged from the wearer.

Figure 3:
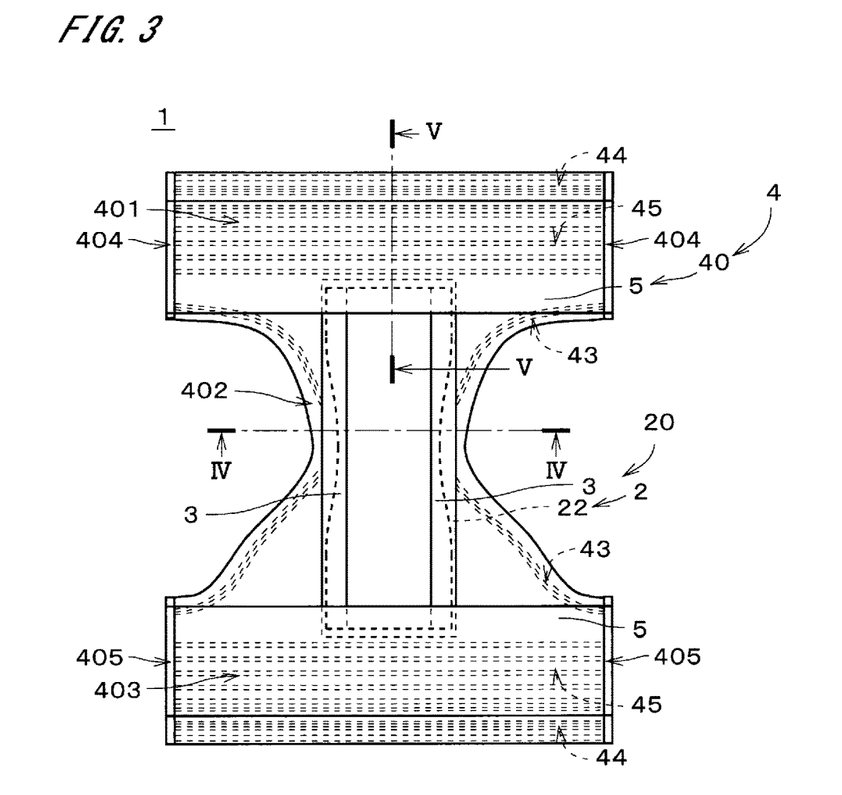
FIG. 3 is a plan view of the expanded disposable diaper.

FIG. 3 is a plan view of the laid out disposable diaper 1 viewed from the wearer side. The disposable diaper 1 includes an outer covering sheet 4 having the waist opening 11 and the pair of leg openings 12 (see FIGS. 1 and 2) and a generally sheet-like absorbent body 20 that is attached to the inner surface of the outer covering sheet 4 (i.e., the surface on the wearer side) and is configured to absorb body waste discharged from the wearer. The outer covering sheet 4 includes an outer covering sheet main body 40, and leg elastic members 43, a waist elastic member 44 and a middle elastic member 45 which are joined to the outer covering sheet main body 40.

In the disposable diaper 1, the area on the upper side in FIG. 3 covers the front side (skin on the belly side) of the wearer, and the area on the lower side in FIG. 3 covers the rear side (skin on the back side) of the wearer. In the following description, areas of the outer covering sheet main body 40 that are located on the belly and back sides of the wearer are respectively referred to as a "front part 401" and a "rear part 403," and an area that is located between and continuous with the front part 401 and the rear part 403 and covers a groin part of the wearer is referred to as a "crotch part 402." In the disposable diaper 1, the outer covering sheet 4 includes the front part 401, the crotch part 402, and the rear part 403, and the absorbent body 20 extends from the front part 401 of the outer covering sheet 4 to the rear part 403 via the crotch part 402.

In the manufacture of the disposable diaper 1, the outer covering sheet 4 is folded at the crotch part 402 together with the absorbent body 20, and the inner surfaces of strip-like areas 404 that are located on both right and left sides of the front part 401 when the crotch part 402 is facing downward are joined to the inner surfaces of strip-like areas 405 that are located on both right and left sides of the rear part 403 by heat sealing through the application of heat and pressure. The inner surfaces of the strip-like areas 404 are surfaces that are laterally continuous with both of the side ends of the inner surface of the front part 401 that comes in contact with the wearer, and are surfaces on the near side in FIG. 3. The inner surfaces of the strip-like areas 405 are surfaces that are laterally continuous with both of the side ends of the inner surface of the rear part 403 that comes in contact with the wearer, and are surfaces on the near side in FIG. 3.

By joining the pair of strip-like areas 404 and the pair of strip-like areas 405 in this way, both of the side ends of the front part 401 and both of the side ends of the rear part 403 are connected as illustrated in FIGS. 1 and 2, forming the waist opening 11 at the upper ends of the front part 401 and the rear part 403. Also, the pair of leg openings 12 is respectively formed on the right and left sides of the crotch part 402 below the front part 401 and the rear part 403, and a pair of strip projecting portions 13 that extend in an up-down direction is formed between the waist opening 11 and the pair of the leg openings 12. The strip projecting portions 13 are each a strip-like area that projects laterally from a line of connection 400 between the front part 401 and the rear part 403.

Figure 4:
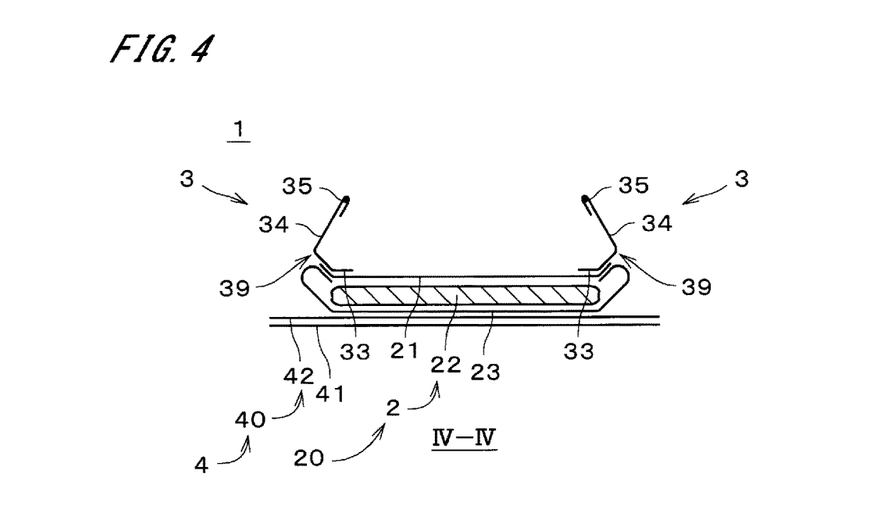
FIG. 4 is a cross-sectional view of the disposable diaper.

FIG. 4 is cross-sectional view of the disposable diaper 1, taken along line IV-IV (i.e., at the crotch part 402) in FIG. 3. In FIG. 4, for convenience of illustration, constituent elements of the disposable diaper 1 are illustrated separately from one another. As illustrated in FIGS. 3 and 4, the absorbent body 20 includes a generally sheet-like main body part 2 and a pair of side sheets 3 that is disposed on both side portions of the main body part 2 (i.e., both sides in a right-left direction perpendicular to the up-down direction) and that extends along approximately the entire longitudinal length of the main body part 2. The main body part 2 includes a top sheet 21, a back sheet 23, and an absorbent core 22 disposed between the top sheet 21 and the back sheet 23 as illustrated in FIG. 4. In order to facilitate understanding of the illustration, the contour of the absorbent core 22 of the absorbent body 20 is shown by the bold broken line in FIG. 3 (the same applies to FIGS. 1 and 2).

As illustrated in FIG. 3, the width of the absorbent core 22 at its both end portions in a longitudinal direction is greater than the width of the absorbent core 22 at its central portion in the longitudinal direction. In other words, the absorbent core 22 has a so-called hourglass shape. The back sheet 23 in FIG. 4 is joined to the outer covering sheet 4 with a hot-melt adhesive or the like, and accordingly the absorbent body 20 is fixed to the outer covering sheet 4.

As illustrated in FIG. 4, the pair of side sheets 3 each includes a strip-like joining part 33 and a side wall part 34, the strip-like joining part 33 being an area on one side of a folding line 39 that extends along the entire length in the longitudinal direction, and the side wall part 34 being an area on the other side of the folding line 39. The pair of joining parts 33 is joined with a hot-melt adhesive to the upper side (i.e., the wearer side) of the main body part 2 along approximately the entire longitudinal length in the vicinity of lateral edges of the main body part 2. The pair of side wall parts 34 corresponds to areas that are continuous with the pair of joining parts 33 at the outer edges of the joining parts 33 in the right-left direction, i.e., the folding lines 39, and extend along approximately the entire longitudinal length of the main body part 2 on both side portions of the main body part 2.

The pair of side wall parts 34 is overlaid on the joining parts 33 at both end portions in the longitudinal direction and is fixed to the joining parts 33 by, for example, heat seal bonding, ultrasonic bonding, or bonding with a hot-melt adhesive. Side wall elastic members 35 are joined to free edges of the side wall parts 34, and the side wall elastic members 35 are configured to contract to form gathers.

Figure 5:
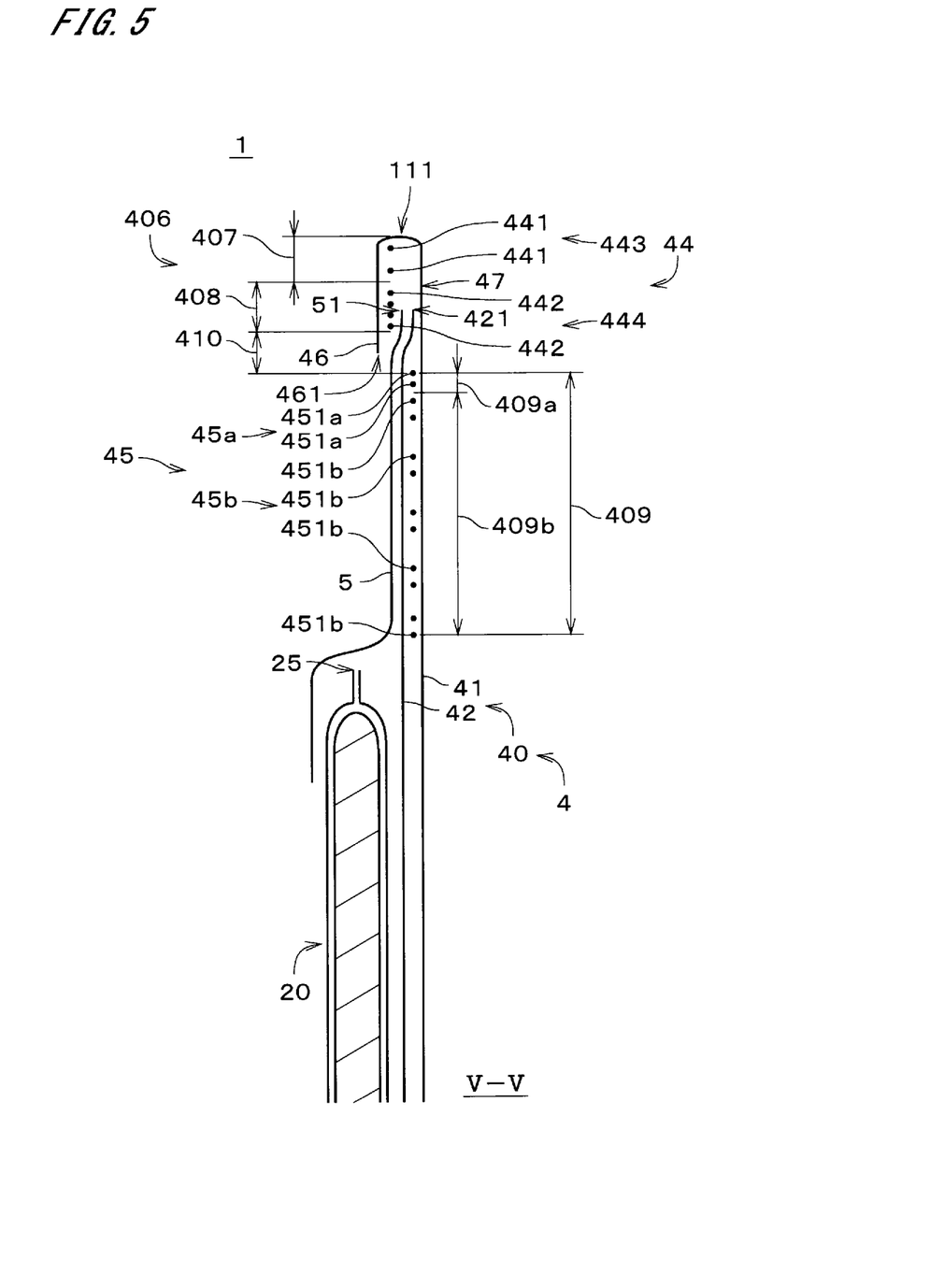
FIG. 5 is a partial cross-sectional view of the disposable diaper.

FIG. 5 is a partial cross-sectional view of the disposable diaper 1, taken along line V-V in FIG. 3. FIG. 5 shows the front side of the disposable diaper 1. The rear-side structure of the disposable diaper 1 is the same as the front-side structure shown in FIG. 5. As illustrated in FIGS. 4 and 5, the outer covering sheet main body 40 of the outer covering sheet 4 includes a first outer covering sheet 41 and a second outer covering sheet 42 that is directly laminated on the inner surface (i.e., the wearer side) of the first outer covering sheet 41 and joined thereto with a hot-melt adhesive or the like.

As illustrated in FIG. 5, the outer covering sheet main body 40 further includes an end sheet 5 that is directly laminated on the inner surface of the second outer covering sheet 42 and joined thereto with a hot-melt adhesive or the like. The end sheet 5 is provided along approximately the entire width of the outer covering sheet 4 in the right-left direction of the disposable diaper 1 (i.e., the lateral direction in FIG. 3) as illustrated in FIG. 3 and sandwiches the upper end portion of the absorbent body 20 between itself and the second outer covering sheet 42 to fix the absorbent body 20 as illustrated in FIG. 5.

An upper end 421 of the second outer covering sheet 42 is at approximately the same level in the up-down direction as an upper end 51 of the end sheet 5 and is spaced from and downward of an edge 111 of the waist opening 11, which is an upper end of the first outer covering sheet 41. The upper end 421 of the second outer covering sheet 42 and the upper end 51 of the end sheet 5 are located above an upper end 25 of the absorbent body 20.

The top sheet 21 of the absorbent body 20 illustrated in FIG. 4 is a liquid-permeable sheet material that quickly catches moisture in body waste discharged from the wearer and moves the moisture to the absorbent core 22. As the top sheet 21, liquid-permeable nonwoven fabric (e.g., point-bonded nonwoven fabric, air-through nonwoven fabric, or spun-bonded nonwoven fabric) is used, for example, which is formed from hydrophobic fibers (e.g., polypropylene, polyethylene, polyester, polyamide, or nylon) having a surface that has undergone hydrophilic treatment using a surfactant. Alternatively, nonwoven fabric (e.g., spunlace nonwoven fabric) formed from hydrophilic fibers such as cellulose, rayon, or cotton may be used for the top sheet 21.

The absorbent core 22 is formed by mixing super-absorbent material such as granular super-absorbent polymer (SAP) or super-absorbent fibers with hydrophilic fibers such as comminuted pulp fibers or cellulose fibers and then wrapping the mixture in tissue paper, a liquid-permeable nonwoven fabric, or the like. The absorbent core 22 absorbs and quickly traps moisture permeating through the top sheet 21. The tissue paper, liquid-permeable nonwoven fabric, or the like that is wrapped around the hydrophilic fibers is joined to the hydrophilic fibers and water-absorbent material with a hot-melt adhesive, thereby preventing deformation of the hydrophilic fibers and detachment of the water-absorbent material (in particular, detachment after water absorption). In the present embodiment, the absorbent core 22 includes pulp fibers and SAP.

As the back sheet 23, water-repellent or liquid-impervious nonwoven fabric formed from hydrophobic fibers (e.g., spunbond nonwoven fabric, meltblown nonwoven fabric, or spunbond-meltblown-spunbond (SMS) nonwoven fabric) or a water-repellent or liquid-impervious plastic film is used to prevent moisture or the like in body waste that has reached the back sheet 23 from leaking to the outside of the main body part 2. In the case of using a plastic film for the back sheet 23, it is preferable to use a permeable (breathable) plastic film from the viewpoint of preventing the disposable diaper 1 from becoming sweaty and improving the comfort of the wearer.

As a sheet main body of the side sheet 3, water-repellent or liquid impermeable nonwoven fabric formed from hydrophobic fibers (e.g., spun-bonded nonwoven fabric, meltblown nonwoven fabric, or SMS nonwoven fabric) is used. As the side wall elastic members 35, polyurethane yarn, a strip-like polyurethane film, or filiform or strip-like natural rubber is used, for example. In the present embodiment, polyurethane yarn is used for the side wall elastic members 35.

Similarly to the back sheet 23, as the first outer covering sheet 41 and the second outer covering sheet 42 of the outer covering sheet main body 40 and the end sheet 5 illustrated in FIG. 5, water-repellent or liquid impermeable nonwoven fabric formed from hydrophobic fiber or plastic films are used, or laminated sheets where such nonwoven fabric and plastic film are laminated, are used. It is preferable to use the plastic films having vapor permeability (breathability). Alternatively, as the first outer covering sheet 41, the second outer covering sheet 42, and the end sheet 5, similarly to the top sheet 21, nonwoven fabric formed from hydrophilic fibers or liquid-permeable nonwoven fabric formed from hydrophobic fibers that have undergone hydrophilic treatment may be used.

In a preferable example, the disposable diaper 1 uses spun-bonded nonwoven fabric, which is formed by melting a material that contains a thermoplastic resin (e.g., an olefin resin or a polyester resin) and a surfactant, for the first outer covering sheet 41 and the second outer covering sheet 42. Here, the compounding ratio of the surfactant in the material is preferably 0.5 percent by mass or higher, and more preferably 1.0 percent by mass or higher, and is preferably 5.0 percent by mass or less, and more preferably 3.5 percent by mass or less. The olefin resin is preferably polyethylene or polypropylene, and the polyester resin is preferably polyethyleneterephthalate (PET), polybutyleneterephtalate (PBT), or polytrimethyleneterephtalate (PTT). The fineness of the nonwoven fabric is preferably 1.0 dtex or higher and is preferably lower than 1.5 dtex. The weight of the nonwoven fabric is preferably 10 g/m² or more and is preferably 35 g/m² or less. From the viewpoint of breathability and strength, the weight of the nonwoven fabric is more preferably 15 g/m² or more and is more preferably 25 g/m² or less.

The first outer covering sheet 41 of the outer covering sheet 4 includes a folded portion 46 formed by folding the first outer covering sheet 41 toward the wearer at the edge 111 of the waist opening 11. A lower end 461 of the folded portion 46 is located below the upper end 421 of the second outer covering sheet 42 and the upper end 51 of the end sheet 5 and is located above the upper end 25 of the absorbent body 20. An upper end portion of the second outer covering sheet 42 and an upper end portion of the end sheet 5 are sandwiched between the folded portion 46 and an opposing portion 47 that is an area of the first outer covering sheet 41 that faces the folded portion 46. The folded portion 46 is joined to the opposing portion 47 and the upper end portion of the end sheet 5.

Between the folded portion 46 and the opposing portion 47 and along the edge 111 of the waist opening 11 is disposed a waist elastic member 44 that extends in the right-left direction as shown in FIG. 3 and is joined to the front part 401 and the rear part 403. In the disposable diaper 1, contraction of the waist elastic member 44 causes contraction of the outer covering sheet main body 40, thereby forming waist opening gathers that come in contact with the wearer. In the present embodiment, the waist elastic member 44 includes six elastic threads as shown in FIG. 5. In the following description, two of these elastic threads that are closest to the edge 111 of the waist opening 11, which is an upper end of the folded portion 46, are referred to as "first elastic threads 441," and the other four elastic threads located below the first elastic threads 441 are referred to as "second elastic threads 442." The two first elastic threads 441 are also collectively referred to as a "first waist elastic member 443," and the four second elastic threads 442 are also collectively referred to as a "second waist elastic member 444." In other words, the waist elastic member 44 includes the first waist elastic member 443 that is disposed approximately in parallel with the edge 111 of the waist opening 11, and the second waist elastic member 444 that is disposed approximately in parallel with the first waist elastic member 443.

The two first elastic threads 441 are arranged in the up-down direction and extend approximately in parallel with the edge 111 of the waist opening 11. The four second elastic threads 442 are arranged at approximately an equal pitch in the up-down direction and extend approximately in parallel with the plurality of first elastic threads 441. The pitch in the up-down direction between the first elastic threads 441, or in other words, a distance in the up-down direction between the two first elastic threads 441, is greater than the pitch in the up-down direction between the second elastic threads 442, or in other words, a distance in the up-down direction between any two second elastic threads 442 that are adjacent to each other in the up-down direction. In this way, the pitch of the first elastic threads 441 and the pitch of the second elastic threads 442 differ from each other. The pitch of the first elastic threads 441 and the pitch of the second elastic threads 442 are respectively 7 mm and 3.5 mm, for example. A distance in the up-down direction between the lower first elastic thread 441 and the uppermost second elastic thread 442 is approximately equal to the distance in the up-down direction between the two first elastic threads 441 (i.e., the pitch of the first elastic threads 441).

The two first elastic threads 441 and the upper two second elastic threads 442 among the four second elastic threads 442 are disposed between the folded portion 46 and the opposing portion 47 of the first outer covering sheet 41 above the upper end 421 of the second outer covering sheet 42 and the upper end 51 of the end sheet 5, and are directly joined to the folded portion 46 and the opposing portion 47. The lower two second elastic threads 442 among the four second elastic threads 442 are disposed between the folded portion 46 and the end sheet 5 below the upper end 421 of the second outer covering sheet 42 and the upper end 51 of the end sheet 5, and are directly joined to the folded portion 46 and the end sheet 5.

If a region of the outer covering sheet 4 where the waist elastic member 44 is disposed is referred to as a "waist region 406", and in the waist region 406 which is a strip-like region extending along the edge 111 of the waist opening 11, regions on which the first waist elastic member 443 and the second waist elastic member 444 are respectively disposed are respectively referred to as a "first waist region 407" and a "second waist region 408", the first waist region 407 is a strip-like upper region of the waist region 406, and the second waist region 408 is a strip-like lower region of the waist region 406 and is located below the first waist region 407.

As described above, the waist region 406 is formed by laminating a plurality of sheet members that include the folded portion 46 and the opposing portion 47 of the first outer covering sheet 41, the second outer covering sheet 42, and the end sheet 5. The first waist region 407 and the upper part of the second waist region 408 are formed by the folded portion 46 and the opposing portion 47 of the first outer covering sheet 41, and the lower part of the second waist region 408 is formed by the folded portion 46, the opposing portion 47, the second outer covering sheet 42, and the end sheet 5. In other words, the number of sheet members in the first waist region 407 is two and less than the number (i.e., four) of sheet members in the lower part of the second waist region 408.

Specifically, the first waist region 407 is a region that extends in the up-down direction from the edge 111 of the waist opening 11 to the middle of the distance in the up-down direction between the lower first elastic thread 441 and the uppermost second elastic thread 442. The second waist region 408 is a region that extends from the middle of the distance in the up-down direction between the lower first elastic thread 441 and the uppermost second elastic thread 442 (i.e., the lower end of the first waist region 407) to a position that is downwardly distant from the lowermost second elastic threads 442 by a distance equivalent to a half of the pitch of the second elastic threads 442. The lower end of the second waist region 408 is located above the lower end 461 of the folded portion 46 (see FIG. 5). The waist region 406 is located above the upper end 25 of the absorbent body 20 and preferably has a width of 50 mm or less in the up-down direction.

As illustrated in FIGS. 1 and 2, the leg elastic members 43 are disposed along edges 121 of the pair of leg openings 12 and joined between the first and second outer covering sheets 41 and 42 of the outer covering sheet 4 (see FIG. 4). The upper end portions of each of the leg elastic member 43 on both sides are joined to the front part 401 and the rear part 403, and the central part of each of the leg elastic members 43 between the upper end portions is joined to the crotch part 402 of the outer covering sheet main body 40. The leg elastic members 43 each include a plurality of leg elastic threads 431. In the disposable diaper 1, contraction of the leg elastic members 43 causes contraction of the outer covering sheet main body 40, thereby forming leg gathers that come in contact with the circumference of the legs of the wearer.

The middle elastic member 45 is disposed between the waist elastic member 44 and the upper end portions of the leg elastic members 43 in the up-down direction, extends in the right-left direction, and is joined to the front part 401 and the rear part 403. As illustrated in FIG. 5, the middle elastic member 45 is disposed between the first outer covering sheet 41 and the second outer covering sheet 42. The middle elastic member 45 includes a plurality of (in the present embodiment, 12) middle elastic threads 451a and 451b that are arranged in the up-down direction and extend approximately in parallel with the first and second elastic threads 441 and 442 of the waist elastic member 44. In the following description, the upper two of the middle elastic threads that are closest to the second elastic threads 442 are referred to as "first middle elastic threads 451a," and the lower ten of the middle elastic threads that are located below first middle elastic threads 451a are referred to as "second middle elastic threads 451b." The two first middle elastic threads 451a are also collectively referred to as a "first middle elastic member 45a", and the ten second middle elastic threads 451b are also collectively referred to as a "second middle elastic member 45b." In other words, the middle elastic member 45 includes the first middle elastic member 45a that is disposed approximately in parallel with the edge 111 of the waist opening 11, and the second middle elastic member 45b that is disposed approximately in parallel with the first middle elastic member 45a.

In the present embodiment, the interval between the two first middle elastic threads 451a is 3.5 mm. The interval between any two second middle elastic threads 451b that are adjacent to each other alternately changes between 7 mm and 14 mm in the up-down direction. In other words, taking any two second middle elastic threads 451b that are disposed at an interval of 7 mm as a pair of second middle elastic threads, the plurality of pairs of second middle elastic threads are disposed at an interval of 14 mm. As described above, the regularity of arrangement of the plurality of first middle elastic threads 451a in the up-down direction differs from that of the plurality of second middle elastic threads 451b. Note that the second middle elastic threads 451b may be disposed at a fixed pitch in the up-down direction.

In the disposable diaper 1, contraction of the middle elastic member 45 causes contraction of the outer covering sheet main body 40, thereby forming middle gathers that come in contact with the lower abdominal and hip regions of the wearer. In the following description, a strip-like region of the outer covering sheet 4 where the middle elastic member 45 is disposed is referred to as a "middle elastic region 409." Specifically, the middle elastic region 409 is defined as a region that extends in the up-down direction from the uppermost first middle elastic thread 451a to the lowermost second middle elastic thread 451b. Similarly to the waist region 406, the middle elastic region 409 is also located above the upper end 25 of the absorbent body 20.

Assuming that in the strip-like middle elastic region 409 extending approximately in parallel with the edge 111 of the waist opening 11, regions where the first middle elastic member 45a and the second middle elastic member 45b are respectively disposed are respectively referred to as a "first middle elastic region 409a" and a "second middle elastic region 409b", the first middle elastic region 409a is a strip-like upper region of the middle elastic region 409, and the second middle elastic region 409b is a strip-like lower region of the middle elastic region 409 and located below the first middle elastic region 409a. Specifically, the first middle elastic region 409a is a region that extends in the up-down direction from the uppermost first middle elastic thread 451a to the middle of the distance between the lower first middle elastic thread 451a and the uppermost second middle elastic thread 451b. The second middle elastic region 409b is a region that extends in the up-down direction from the middle of the distance between the lower first middle elastic thread 451a and the uppermost second middle elastic thread 451b (i.e., the lower end of the first middle elastic region 409a) to the lowermost second middle elastic thread 451b.

Between the second waist region 408 and the middle elastic region 409 of (the outer covering sheet main body 40 of) the outer covering sheet 4 is provided an auxiliary region 410 that has no elastic members disposed therein. An upper end of the auxiliary region 410 is in contact with the lower end of the second waist region 408, and a lower end of the auxiliary region 410 is in contact with the upper end of the middle elastic region 409. The width of the auxiliary region 410 in the up-down direction is preferably two times or more of the pitch of the second elastic threads 442, and more preferably three times or more of the pitch of the second elastic threads 442, and is less than or equal to the width of the waist region 406 in the up-down direction. In the present embodiment, the auxiliary region 410 has a width of 10 mm. In the disposable diaper 1, all of the first and second elastic threads 441 and 442 of the waist elastic member 44 and all of the first middle elastic threads 451a of the first middle elastic member 45a are colored differently from the elastic threads of the other elastic members (i.e., the second middle elastic member 45b and the leg elastic members 43). Specifically, the elastic threads of the other elastic members have a color of the same hue (e.g., white) as the outer covering sheet main body 40, whereas the first and second elastic threads 441 and 442 and the first middle elastic threads 451a have a color of different hue from that of the outer covering sheet main body 40. Thus, roughly the upper end of the auxiliary region 410 is visually recognizable by the second elastic threads 442 in the vicinity of the lower end of the second waist region 408, and the lower end of the auxiliary region 410 is visually recognizable by the first middle elastic threads 451a at the upper end of the middle elastic region 409. Accordingly, the auxiliary region 410 is substantially visually recognizable. Alternatively, the auxiliary region 410 may be made visually recognizable by, for example, printing a strip-like pattern extending in the right-left direction on the auxiliary region 410 of the outer covering sheet main body 40.

In the present embodiment, the plurality of first elastic threads 441 and the plurality of second elastic threads 442 of the waist elastic member 44, the plurality of leg elastic threads 431 of the leg elastic members 43 (see FIGS. 1 and 2), and the plurality of middle elastic threads 451a and 451b of the middle elastic member 45 are all polyurethane yarns having the same elastic modulus and the same fineness. The fineness of the polyurethane yarns is in the range of 100 to 2500 dtex, for example. These elastic threads may, of course, have different finenesses, and in another preferable example, the disposable diaper 1 may use first and second elastic threads 441 and 442 having a fineness of 940 dtex and middle elastic threads 451a and 451b having a fineness of 640 dtex.

These elastic threads are fixed to the outer covering sheet main body 40 by heat seal bonding or bonding with a hot-melt adhesive. Preferably, the first elastic threads 441 are fixed to the outer covering sheet main body 40 with an adhesive applied to the first elastic threads 441. More preferably, no adhesive is applied to the first waist region 407 itself of the outer covering sheet main body 40 (the first outer covering sheet 41 and the folded portion 46) from the viewpoint of improving the texture of the edge of the waist opening 1. On the other hand, in the second waist region 408, an adhesive may be applied to both or one of the second elastic threads 442 and the second waist region 408 of the outer covering sheet main body 40. In the present embodiment, an adhesive is applied to the second waist region 408 of the folded portion 46 to fix the folded portion 46 to the opposing portion 47 and the upper end portion of the end sheet 5, and no adhesive is applied to the first waist region 407 itself and to the auxiliary region 410 itself. Preferably, from the viewpoint of improving breathability in the middle elastic region 409, the middle elastic threads 451a and 451b of the middle elastic member 45 are fixed to the outer covering sheet main body 40 with an adhesive applied to the middle elastic threads 451a and 451b, without any adhesive being applied to the middle elastic region 409 itself of the outer covering sheet main body 40. In this case, it is possible to further improve breathability by applying an adhesive to some of the middle elastic threads 451a and 451b, only in areas in the vicinity of the pair of strip projecting parts 13, i.e., only at both end portions of some of the middle elastic threads 451a and 451b.

The elongation rate of the first elastic threads 441 when joined to the first waist region 407 is equal to the elongation rate of the second elastic threads 442 when joined to the second waist region 408. The number of first elastic threads 441 per unit width of the first waist region 407 in the up-down direction, that is, a value obtained by dividing the total number of first elastic threads 441 by the width of the first waist region 407 in the up-down direction, is less than the number of second elastic threads 442 per unit width of the second waist region 408 in the up-down direction. Thus, in a state in which the outer covering sheet 4 is elongated in the right-left direction (e.g., in a state in which the disposable diaper 1 is worn), a first unit contractile force that is a contractile force in the right-left direction per unit width of the first waist region 407 in the up-down direction is smaller than a second unit contractile force that is a contractile force in the right-left direction per unit width of the second waist region 408 in the up-down direction.

Accordingly, the second waist region 408 of the waist region 406 closely fits the waist area of the wearer, the first waist region 407 comes into relatively soft contact with the waist area of the wearer. As a result, cutting in of the upper end portions of the pair of strip projecting parts 13 into the skin of the wearer can be suppressed. In addition, by setting a relatively large second unit contractile force while setting a relatively small first unit contractile force so as to maintain the contractile force in the entire waist region 406, it is possible to closely fit the first waist region 407 and the second waist region 408 to the wearer and to prevent the disposable diaper 1 from slipping off in the up-down direction when being worn. The first unit contractile force is preferably 70% or less of the second unit contractile force, and in the present embodiment, the first unit contractile force is approximately 50% of the second unit contractile force.

Here, when a pants-type disposable diaper is put on or taken off, the wearer's feet are put into the pair of leg openings of the disposable diaper and then the disposable diaper is pulled up along the body of a wearer, or the disposable diaper being worn by the wearer is pulled down along the body of the wearer. At this time, the waist opening is widened in order to avoid the edge of the waist opening catching on part of the body of the wearer. In such a case, in the disposable diaper 1 in which the first unit contractile force is smaller than the second unit contractile force, the edge of the waist opening 11 can be widened by a small force. It is thus possible to easily move the disposable diaper 1 along the body of the wearer.

From the viewpoint of preventing the disposable diaper 1 from slipping off in the up-down direction when being worn, the contractile force per unit width of the entire waist region 406 is preferably 1 cN/mm or more (more preferably, 2 cN/mm or more). The contractile force per unit width of the entire waist region 406 is measured as described below, using a "TENSILON (model type: RTG-1210)" manufactured by A&D Co., Ltd. as a measuring machine. Note that the first unit contractile force, the second unit contractile force, and a middle unit contractile force which will be described later, are also measured by the same method.

First, a test specimen is obtained by cutting out the waist region 406 of the disposable diaper 1 along the entire width thereof in the up-down direction. Next, both ends of the test specimen in the right-left direction (i.e., the direction in which the first elastic threads 441 and the second elastic threads 442 extend) are held by clamp portions of the measuring machine, and the test specimen is pulled in the right-left direction, and the load until the test specimen returns to its original shape is measured. At this time, the test specimen is pulled to up to 90% of the length in the right-left direction of a test specimen that is not provided with the first elastic threads 441 and the second elastic threads 442 (i.e., the length of a test specimen that does not contract). The pulling of the test specimen and measurement of load are repeated a plurality of times. Then, the measurement results are used to obtain the load at the time when the length of the test specimen is 180% of the length of the test specimen before being pulled (i.e., the length of the test specimen that contracts due to the first elastic threads 441 and the second elastic threads 442) and to obtain an average load that is an average value of the loads obtained by the plurality of measurements. Then, the average load is divided by the width of the test specimen in the up-down direction so as to obtain the contractile force per unit width of the test specimen.

As described above, in the outer covering sheet 4, the number of sheet members in the first waist region 407 is reduced to less than the number of sheet members in the second waist region 408. This reduces the number of sheet members constituting the upper end portions of the pair of strip projecting parts 13, thus making it possible to reduce stiffness. As a result, it is possible to further suppress cutting in of the upper end portions of the pair of strip projecting parts 13 into the skin of the wearer. In addition, the edge of the waist opening 11 can be widened by a small force.

The folded portion 46 is formed by folding the first outer covering sheet 41 of the outer covering sheet 4 at the edge 111 of the waist opening 11, and the waist elastic member 44 is disposed between the folded portion 46 and the opposing portion 47. In this way, the edge 111 of the waist opening 11 and the upper end portions of the pair of strip projecting parts 13 are formed by the fold in the continuous sheet member. It is thus possible to further suppress cutting in of them into the skin of the wearer, as compared with the case in which a cut edge of the sheet member forms the edge 111 of the waist opening 11 and the upper end portions of the strip projecting parts 13. Moreover, in the waist region 406, the pitch in the up-down direction between the plurality of first elastic threads 441 is made greater than the pitch in the up-down direction between the plurality of second elastic threads 442. Thus, the first unit contractile force in the first waist region 407 can be readily reduced to smaller than the second unit contractile force in the second waist region 408.

In the disposable diaper 1, the elongation rate of the middle elastic threads 451a and 451b when joined to the middle elastic region 409 is equal to or lower than the elongation rate of the first elastic threads 441 when joined to the first waist region 407. The number (average number) of middle elastic threads 451a and 451b per unit width of the middle elastic region 409 in the up-down direction is less than the number of first elastic threads 441 per unit width of the first waist region 407 in the up-down direction. Thus, in the state in which the outer covering sheet 4 is elongated in the right-left direction, the middle unit contractile force that is an average contractile force in the right-left direction per unit width of the middle elastic region 409 in the up-down direction is smaller than the first unit contractile force and the second unit contractile force described above. Accordingly, in the middle elastic region 409, the disposable diaper 1 can closely fit the wearer while preventing the skin of the wearer from being excessively compressed.

As described above, in the outer covering sheet 4, no elastic members are disposed in the auxiliary region 410 located between the second waist region 408 and the middle elastic region 409. Accordingly, in the state in which the outer covering sheet 4 is elongated in the right-left direction, the contractile force in the right-left direction per unit width of the auxiliary region 410 in the up-down direction is smaller than any of the middle unit contractile force, the first unit contractile force, and the second unit contractile force. This allows the disposable diaper 1, when being put on or taken off, to be easily and firmly grasped by hooking fingers deep into the auxiliary region 410, enabling the disposable diaper 1 to be easily moved along the body of the wearer. The auxiliary region 410 can be easily recognized and used because it is visually recognizable. From the viewpoint of hooking fingers into the auxiliary region 410, the auxiliary region 410 preferably has a width of 7 mm or more in the up-down direction.

In the case where the middle elastic region 409 is segmented into the first middle elastic region 409a and the second middle elastic region 409b, the elongation rate of the first middle elastic threads 451a when joined to the first middle elastic region 409a is equal to the elongation rate of the second middle elastic threads 451b when joined to the second middle elastic region 409b. The number of first middle elastic threads 451a per unit width of the first middle elastic region 409a in the up-down direction is greater than the number of second middle elastic threads 451b per unit width of the second middle elastic region 409b in the up-down direction. Accordingly, in the state in which the outer covering sheet 4 is elongated in the right-left direction, the contractile force in the right-left direction per unit width of the first middle elastic region 409a in the up-down direction is greater than the contractile force in the right-left direction per unit width of the second middle elastic region 409b in the up-down direction.

Because the contractile force in the first middle elastic region 409a adjacent to the auxiliary region 410 is greater than the contractile force in the second middle elastic region 409b located below the first middle elastic region 409a, the first middle elastic region 409a readily tracks and pulls up around its entire circumference when part of the auxiliary region 410 is pulled up at the time of putting on or taking off the disposable diaper 1 in which a great force acts locally on the auxiliary region 410, thus enabling the disposable diaper 1 to be smoothly pulled up. In addition, in the disposable diaper 1, the contractile force in the first middle elastic region 409a can be easily made greater than the contractile force in the second middle elastic region 409b by setting the elongation rates of the first middle elastic threads 451a and the second middle elastic threads 451b in joining to the same value and setting the pitch in the up-down direction between the first middle elastic threads 451a to be smaller than the pitch (average pitch) between the second middle elastic threads 451b.

Preferably, the elongation rate of the first middle elastic threads 451a when joined to the first middle elastic region 409a is equal to the elongation rate of the second elastic threads 442 when joined to the second waist region 408, and the number of first middle elastic threads 451a per unit width of the first middle elastic region 409a in the up-down direction is approximately equal to the number of second elastic threads 442 per unit width of the second waist region 408 in the up-down direction. Accordingly, in the state in which the outer covering sheet 4 is elongated in the right-left direction, the contractile force in the right-left direction per unit width of the first middle elastic region 409a in the up-down direction is approximately equal to the second unit contractile force in the second waist region 408 (e.g., the difference between these contractile forces is 10% or less of one of the contractile forces). This allows the second waist region 408 and the first middle elastic region 409a located on both sides of the auxiliary region 410 in the up-down direction to closely fit the skin of the wearer at approximately the same pressure and prevents the skin of the wearer from being compressed locally. In the disposable diaper 1, the contractile force in the first middle elastic region 409a can be readily made equal to the second unit contractile force in the second waist region 408 by setting the elongation rates of the first middle elastic threads 451a and the second elastic threads 442 when joined to the same elongation rate and setting the pitch in the up-down direction between the first middle elastic threads 451a and the pitch in the up-down direction between the second elastic threads 442 to the same pitch.

In the disposable diaper 1, the numbers of the first elastic threads 441 and the second elastic threads 442 may be appropriately changed as long as the first unit contractile force is smaller than the second unit contractile force. For example, in the case where the first waist elastic member 443 includes only one first elastic thread 441, the upper end of the first waist region 407 is the edge 111 of the waist opening 11, and the lower end of the first waist region 407 is at a position in the middle of the distance in the up-down direction between the first elastic thread 441 and the uppermost second elastic thread 442. In the case where the second waist elastic member 444 includes only one second elastic thread 442, the upper end of second waist region 408 is at a position in the middle of the distance in the up-down direction between the second elastic thread 442 and the lowermost first elastic thread 441, and the lower end of the second waist region 408 is at a position distant from and below the second elastic thread 442 by the distance in the up-down direction between the upper end and the second elastic thread 442. Similarly, the number of first middle elastic threads 451a and second middle elastic threads 451b may be changed.

As described above, in the disposable diaper 1, the first unit contractile force in the first waist region 407 is reduced to smaller than the second unit contractile force in the second waist region 408 by setting the pitch of the plurality of first elastic threads 441 in the up-down direction to be greater than the pitch of the plurality of second elastic threads 442 in the up-down direction. However, in the case where the first unit contractile force is reduced to smaller than the second unit contractile force by other methods, the pitch of the first elastic threads 441 may be smaller than or equal to the pitch of the second elastic threads 442 (the same applies to the pitch of the first middle elastic threads 451a and the pitch of the second middle elastic threads 451b).

For example, in the disposable diaper 1, the first unit contractile force may be reduced to smaller than the second unit contractile force by setting the elongation rate of each first elastic thread 441 when the plurality of first elastic threads 441 of the first waist elastic member 443 are joined to the first waist region 407 to be lower than the elongation rate of each second elastic thread 442 when the plurality of second elastic threads 442a of the second waist elastic member 444 are joined to the second waist region 408. In this case as well, the first unit contractile force can be reduced to smaller than the second unit contractile force. Similarly, the contractile force in the first middle elastic region 409a may be made greater than the contractile force in the second middle elastic region 409b by setting the elongation rate of each first middle elastic thread 451a when the plurality of first middle elastic threads 451a of the first middle elastic member 45a are joined to the first middle elastic region 409a to be higher than the elongation rate of each second middle elastic thread 451b when the plurality of second middle elastic threads 451b of the second middle elastic member 45b are joined to the second middle elastic region 409b. The elongation rates of these elastic threads are preferably in the range of 1.1 times to 5.0 times, for example.

Alternatively, the first unit contractile force may be reduced to smaller than the second unit contractile force by using, as the first waist elastic member 443, first elastic threads 441 that have a lower elastic modulus than that of the second elastic threads 442 of the second waist elastic member 444, or first elastic threads 441 that have a lower fineness than that of the second elastic threads 442. In either case, the first unit contractile force can be readily reduced to smaller than the second unit contractile force. Similarly, the contractile force in the first middle elastic region 409a may be easily made greater than the contractile force in the second middle elastic region 409b by using, as the first middle elastic member 45a, first middle elastic threads 451a that have a higher elastic modulus than that of the second middle elastic threads 451b of the second middle elastic member 45b, or first middle elastic threads 451a that have a higher fineness than that of the second middle elastic threads 451b.

While the above has been a description of an embodiment of the present invention, the present invention is not limited to the embodiment described above, and various modifications are possible.

In the state in which the outer covering sheet 4 is elongated in the right-left direction, an elastic member may be provided in the auxiliary region 410 as long as the contractile force in the auxiliary region 410 is smaller than any of the middle unit contractile force, the first unit contractile force, and the second unit contractile force.

The leg elastic members 43, the waist elastic member 44, and the middle elastic member 45 may be strip-like polyurethane films, or filiform or strip natural rubber, for example, similarly to the side wall elastic member 35 of the side sheet 3. Preferably, polyurethane yarn covered with fibers is used from the viewpoint of improving the texture of the disposable diaper 1.

While the middle unit contractile force is smaller than the first unit contractile force and the second unit contractile force in the above-described embodiment, the middle unit contractile force may be greater than or equal to the first unit contractile force as long as slipping-off in the up-down direction of the disposable diaper 1, when being worn, is prevented by setting the contractile force per unit width of the entire waist region 406 to an appropriate value.

The structure of the above-described disposable diaper 1 may be used for pants-type absorbent articles other than disposable diapers.

The configurations of the above-described preferred embodiments and variations may be appropriately combined as long as there are no mutual inconsistencies.

While the invention has been shown and described in detail, the foregoing description is in all aspects illustrative and not restrictive. It is therefore understood that numerous modifications and variations can be devised without departing from the scope of the invention.

REFERENCE SIGNS LIST

1 Disposable diaper
4 Outer covering sheet
5 End sheet
11 Waist opening
12 Leg opening
13 Strip projecting part
20 Absorbent body
25 Upper end
43 Leg elastic member
44 Waist elastic member
45 Middle elastic member
45a First middle elastic member
45b Second middle elastic member
46 Folded portion
47 Opposing portion
111, 121 Edge
400 Line of connection
401 Front part
402 Crotch part
403 Rear part
404, 405 Area
406 Waist region
407 First waist region
408 Second waist region
409 Middle elastic region
409a First middle elastic region
409b Second middle elastic region
410 Auxiliary region
441 First elastic thread
442 Second elastic thread
443 First waist elastic member
444 Second waist elastic member

The invention claimed is:

1. A pants-type absorbent article comprising:
an outer covering sheet having a waist opening at an upper end and a pair of leg openings in a lower portion; and
an absorbent body attached to a wearer side of said outer covering sheet to absorb body waste discharged from a wearer, said absorbent body including a top sheet, a back sheet, and an absorbent core disposed between said top sheet and said back sheet,
wherein said outer covering sheet includes:
a front part to be located on a belly side of said wearer;
a rear part to be located on a back side of said wearer, both side ends of said rear part being connected to both side ends of said front part;
a crotch part continuous with said front part and said rear part;
a pair of strip projecting parts formed by joining inner surfaces of areas of said front part that are laterally continuous with said both side ends of said front part and inner surfaces of areas of said rear part that are laterally continuous with said both side ends of said rear part, each of said pair of strip projecting parts having a strip-like shape that extends in an up-down direction and projecting laterally from a line of connection between said front part and said rear part;
a waist elastic member joined to said front part and said rear part in a waist region located along an edge of said waist opening, and configured to contract to form a waist opening gather;
leg elastic members joined to said crotch part along edges of said pair of leg openings and configured to contract to form a pair of leg opening gathers; and
a middle elastic member joined to said front part and said rear part in a space in said up-down direction between said waist elastic member and said leg elastic members, and configured to contract to form a middle gather,
said waist elastic member includes:
a first waist elastic member disposed approximately in parallel with said edge of said waist opening in a first waist region that is an upper part of said waist region; and
a second waist elastic member disposed approximately in parallel with said first waist elastic member in a second waist region that is a region of said waist region below said first waist region,
wherein said first waist elastic member, said second waist elastic member and said middle elastic member are all in contact with a same sheet included in said outer covering sheet and are located above upper ends of said top sheet and said back sheet of said absorbent body, and
in a state in which said outer covering sheet is elongated in a right-left direction perpendicular to said up-down direction, a first unit contractile force that is a contractile force in said right-left direction per unit width of said first waist region in said up-down direction is smaller than a second unit contractile force that is a contractile force in said right-left direction per unit width of said second waist region in said up-down direction.

2. The absorbent article according to claim 1, wherein said waist region has a width of 50 mm or less in said up-down direction.

3. The absorbent article according to claim 1, wherein said outer covering sheet includes a folded portion formed by folding said outer covering sheet toward a wearer at said edge of said waist opening, and
said waist elastic member is disposed between said folded portion and a portion of said outer covering sheet that faces said folded portion.

4. The absorbent article according to claim 1, wherein said waist region is formed by laminating a plurality of sheet members, and
the number of sheet members in said first waist region is less than the number of sheet members in said second waist region.

5. The absorbent article according to claim 1, wherein said first unit contractile force is 70% or less of said second unit contractile force.

6. The absorbent article according to claim 1, wherein said first waist elastic member includes a plurality of first elastic threads that are arranged in said up-down direction and each extend approximately in parallel with said edge of said waist opening,
said second waist elastic member includes a plurality of second elastic threads that are arranged in said up-down direction and each extend approximately in parallel with said plurality of first elastic threads, and
a pitch in said up-down direction between said plurality of first elastic threads is greater than a pitch in said up-down direction between said plurality of second elastic threads.

7. The absorbent article according to claim 1, wherein an elongation rate of said first waist elastic member when joined to said first waist region is lower than an elongation rate of said second waist elastic member when joined to said second waist region.

8. The absorbent article according to claim 1, wherein said first waist elastic member has a lower elastic modulus than an elastic modulus of said second waist elastic member.

9. The absorbent article according to claim 1, wherein said first waist elastic member has a lower fineness than a fineness of said second waist elastic member.

10. The absorbent article according to claim 1, wherein said outer covering sheet includes an auxiliary region between said second waist region and a middle elastic region in which said middle elastic member is disposed, and in a state in which said outer covering sheet is elongated in said right-left direction, a contractile force in said right-left direction per unit width of said auxiliary region in said up-down direction is smaller than any of a contractile force in said right-left direction per unit width of said middle elastic region in said up-down direction, said first unit contractile force, and said second unit contractile force.

11. The absorbent article according to claim 10, wherein said auxiliary region has no elastic member disposed therein.

12. The absorbent article according to claim 10, wherein said auxiliary region is visually recognizable.

13. The absorbent article according to claim 10, wherein said middle elastic member includes:

a first middle elastic member disposed approximately in parallel with said edge of said waist opening in a first middle elastic region that is an upper part of said middle elastic region; and a second middle elastic member disposed approximately in parallel with said first middle elastic member in a second middle elastic region that is a region of said middle elastic region below said first middle elastic region, and in a state in which said outer covering sheet is elongated in said right-left direction, a contractile force in said right-left direction per unit width of said first middle elastic region in said up-down direction is greater than a contractile force in said right-left direction per unit width of said second middle elastic region in said up-down direction.

14. The absorbent article according to claim 13, wherein in a state in which said outer covering sheet is elongated in said right-left direction, the contractile force in said right-left direction per unit width of said first middle elastic region in said up-down direction is approximately equal to said second unit contractile force.

* * * * *